United States Patent [19]
Platt

[11] Patent Number: 5,998,478
[45] Date of Patent: Dec. 7, 1999

[54] TIMED RELEASE TABLET COMPRISING NAPROXEN AND PSEUDOEPHEDRINE

[76] Inventor: Chris E. Platt, 14352 Riviera Dr., Huntington Beach, Calif. 92647

[21] Appl. No.: 09/215,031

[22] Filed: Dec. 17, 1998

Related U.S. Application Data

[63] Continuation of application No. 08/820,174, Mar. 19, 1997, Pat. No. 5,859,060.
[60] Provisional application No. 60/035,517, Jan. 15, 1997.

[51] Int. Cl.⁶ .......................... A61K 31/19; A61K 31/135
[52] U.S. Cl. .............................................. 514/569; 514/653
[58] Field of Search ...................................... 514/569, 653

[56] References Cited

U.S. PATENT DOCUMENTS 4,552,899  11/1985  Sunshine et al. .
4,619,934  10/1986  Sunshine et al. .

*Primary Examiner*—William R. A. Jarvis
*Attorney, Agent, or Firm*—James G. O'Neill

[57] ABSTRACT

Disclosed herein is a pharmaceutical composition comprising naproxen and the decongestant pseudoephedrine in a time release tablet form in the therapy of sinusitis, or sinus headaches, generally exemplified by discomfort, pain, pressure, and dizziness.

1 Claim, No Drawings

TIMED RELEASE TABLET COMPRISING NAPROXEN AND PSEUDOEPHEDRINE

This application is a continuation of application Ser. No. 08/820,174, filed on Mar. 19, 1997 now U.S. Pat. No. 5,859,060 which is a provisional application Ser. No. 60/035,517 filed Jan. 15, 1997.

BACKGROUND OF THE INVENTION

The present invention relates generally to novel pharmaceutical compositions of matter comprising the non-steroidal anti-inflammatory analgesic naproxen in combination with the decongestant pseudoephedrine and appropriate non-toxic carriers and to methods of using said compositions in the therapy or cure of sinusitis, or sinus headaches, generally exemplified by discomfort, pain, pressure, and dizziness.

Non-narcotic analgesics, commonly known as non-steroidal anti-inflammatory drugs, such as naproxen, are widely administered orally in the treatment of mild to severe pain. These drugs have been disclosed as useful in treating cough/cold symptoms in combination with certain antihistamines and decongestants. See, for example U.S. Pat. No. 4,552,899 to Sunshine.

Naproxen as non-steroidal anti-inflammatory pain reliever has greater advantage than other pain relievers acetaminophen, aspirin, and ibuprofen. Naproxen has a significantly greater duration or half-life that leads to twice a day dosage. It is generally accepted that decreased dosing leads to patient convenience and better compliance.

Originally combinations of anti-inflammatories and antihistamines or decongestants were combined with no consideration to the vastly different drug duration or half-lives. These drugs with different half-lives were not combined in a synergistic manner which led the body effectively using them at equal rates. This would lead to ineffective combinations of anti-inflammatories and decongestants and the return of partial symptoms.

SUMMARY OF THE INVENTION

It is a primary object of the present invention to provide a novel timed-release pharmaceutical composition of matter comprising an analgesically effective amount of naproxen and an effective amount of decongestant pseudoephedrine with pharmaceutically acceptable excipients.

It is a further object of the present invention that administration of our specific ratio of composition optimizes the most effective drug level of both drugs in the body over time for relief for nasal sinus congestion that causes headache pain, pressure, dizziness, and general malaise.

DETAILED DESCRIPTION OF THE INVENTION

More specifically, the applicant herein has found that a timed-released combination product suitable for oral administration comprising naproxen and pseudoephedrine combined with or without an appropriate base salt. Through studying extensively the applicant has found that the preferred dosage form that provides for immediate release of naproxen and pseudoephedrine, and specific timed release of pseudoephedrine.

The release of naproxen and pseudoephedrine takes place together up to 12 hours, preferably 10 hours. One or two tablets are administered orally, preferably two. Concentration ranges for the active ingredients are naproxen, 50–500 mg per tablet; pseudoephedrine 30–240 mg per tablet. The concentration ranges represent 7–30% of coated tablet weight of pseudoephedrine and 15–60% of naproxen.

The preferred dosage form is a coated tablet, wherein naproxen and pseudoephedrine are on the outer coating thus released immediately while pseudoephedrine in the core is released over time, preferably over the duration of the half-life of the naproxen, approximately 10 hours. The outer-coating dissolving rapidly to release both naproxen and pseudoephedrine and the inner core dissolves slowly to time release pseudoephedrine through hydration and diffusion of the drug from the core polymer.

The dosage range for naproxen is from 50–800 mg per day depending upon pain management requirements. The range of pseudoephedrine is between 30–240 mg per day depending on blood pressure values and overall health of the patient. Both drugs will vary depending upon the age and weight of the patient, the severity of the symptoms and the incidence of side effects for humans.

The core consists of common hydrophilic swellable polymers such as 25 hydroxypropylmethylcellulose (HPMC) or hydroxypropylcellulose either by themselves or in combination with each other. The hydrated polymers act as a binder that swells when hydrated by gastric media and delays absorption. The combination of polymers will represent about 15% of tablet core weight. The tablet outer coating comprises HPMC and a plasticizer such as polyethylene 30 glycol (PEG) both which dissolve immediately in gastric fluids. Suitable coloring and flavoring agents may be included.

The tablet core also comprises excipients such as polymers, fillers, binders, lubricants, and antiadherents, all necessary for standard tablet manufacture. Binders are present at a concentration of 5% and typically are starch, gelatin, natural or artificial gums. Fillers are present at a concentration of about 10 to 20% of tablet core weight and may include starches or cellulose. Antiadherents used to prevent tablets from sticking to the tablet press typically include silicas and talc, are present from 0 to 6% of the tablet core weight. Typical lubricants are magnesium stearate, boric acid, or sodium benzoate at a concentration of about 2.5% to 5% of the tablet core weight. Additional binders used in the granulation of the drug polymer mixture include povidone and corn starch. Such binders are present at a concentration of about 0.5% to 3% of the tablet core weight.

The means of preparing compositions of the present invention, e.g. tablet mixing, compaction, and coating are all well known to those skilled in the art.

EXAMPLE I

|  | Mg/tablet |
|---|---|
| A. Core Tablet | |
| Pseudoephedrine Sulfate | 30 |
| Microcrystalline Cellulose | 140 |
| Povidone | 15 |
| HPMC/PEG | 40 |
| Magnesium Stearate | 10 |
| B. Outer Coating | |
| Naproxen | 100 |
| Pseudoephedrine Sulfate | 30 |
| HPMC/PEG | 10 |

Method of Manufacture

A. Outer Coating
1. Dissolve HPMC/PEG in an alcohol mixture.
2. Disperse Naproxen and Pseudoephedrine in the HPMCI-PEG solution.
3. Coat inner tablets below with the solution using standard procedures.

B. Inner Core
1. Mix pseudoephedrine sulfate, microcrystalline cellulose and HPMC.
2. Dissolve povidone in an alcoholic mixture and use it to crystallate the powder mix.
3. Dry pseudoephedrine sulfate crystalate mix.
4. Compress into tablets.

While the invention is described and illustrated with reference to certain preferred embodiments thereof, those skilled in the art will appreciate that various changes or modifications can be made therein without departing from the spirit of the invention For example, effective dosages of the active ingredients other than the preferred ranges set forth hereinabove may be used. It is intended that the invention be limited only by the scope of the claims that follow.

I claim:

1. A pharmaceutical composition in the form of a sustained release coated tablet having an inner core and an outer coating, with the inner core comprising from about 15 mg to 120 mg pseudoephedrine sulfate, 140 mg microcrystalline cellulose, 2 mg to 15 mg providone or corn starch, 50 mg of a solution of hydroxypropylmethylcellulose or hydroxypropylcellulose and polyethylene 30 glycol and 6 mg to 11.75 mg magnesium stearate, boric acid or sodium benzoate; and an outer coating comprising from 50 mg to 500 mg naproxen, 15 mg to 120 mg pseudoephedrine sulfate and 10 mg of a solution of hydroxypropylmethylcellulose or hydroxypropylcellulose and polyethylene 30 glycol.

* * * * *